United States Patent [19]

Parr

[11] Patent Number: 4,822,999
[45] Date of Patent: Apr. 18, 1989

[54] APPARATUS AND METHOD FOR DETECTING MOVEMENT OF AN OBJECT

[76] Inventor: David T. Parr, 26 Smithy Brow, Near Warrington, Cheshire, United Kingdom

[21] Appl. No.: 43,696

[22] Filed: Apr. 29, 1987

[30] Foreign Application Priority Data

May 1, 1986 [GB] United Kingdom ............... 8610654

[51] Int. Cl.$^4$ .............................................. H01J 5/16
[52] U.S. Cl. .................................... 250/227; 250/226; 250/231 R; 73/517 R; 73/651; 73/653
[58] Field of Search ................ 250/227, 231 GY, 226; 73/517 R, 651, 653, 652

[56] References Cited

U.S. PATENT DOCUMENTS

| 3,004,531 | 10/1961 | Udale. | |
|---|---|---|---|
| 3,370,472 | 2/1968 | Cunningham | 73/517 R |
| 4,247,202 | 1/1981 | Failes. | |
| 4,278,538 | 7/1981 | Lawrence et al.. | |
| 4,334,152 | 6/1982 | Dakin et al. | 250/226 |
| 4,493,212 | 1/1985 | Nelson | 73/517 R |
| 4,517,456 | 5/1985 | Halsall et al.. | |
| 4,543,961 | 10/1985 | Brown. | |
| 4,547,074 | 10/1985 | Hinoda et al.. | |
| 4,567,771 | 2/1986 | Nelson et al. | 73/517 R |

FOREIGN PATENT DOCUMENTS

| 0014848 | 1/1980 | European Pat. Off.. |
|---|---|---|
| 0102677 | 3/1981 | European Pat. Off.. |
| 0057464 | 2/1982 | European Pat. Off.. |
| 1063023 | 4/1964 | United Kingdom. |
| 1401699 | 11/1972 | United Kingdom. |
| 2016684A | 2/1979 | United Kingdom. |
| 2025608A | 6/1979 | United Kingdom. |
| 2115139A | 2/1982 | United Kingdom. |
| 2141541A | 6/1984 | United Kingdom. |
| 2144534A | 6/1984 | United Kingdom. |
| 2147414A | 9/1984 | United Kingdom. |
| 2160310A | 6/1985 | United Kingdom. |
| 2165043A | 8/1985 | United Kingdom. |

Primary Examiner—Edward P. Westin
Assistant Examiner—Khaled Shami
Attorney, Agent, or Firm—Anthony J. Casella; Gerald E. Hespos

[57] ABSTRACT

The movement of a body (1) is determined by mounting on or in the body one or more sources (3,4) and one or more detectors (12,14) such that each source propagates polychromatic light along a path to a detector. Radiation modulation means (19;25) is supported by the body such that a change in the movement of the body causes a displacement of the radiation modulation means in at least one light path to vary the distributed spectral content of the light reaching the detector. The or each detector is adapted to detect the intensity of incident radiation at a plurality of different wavelengths, and analysis means (18) interprets the output of each detector in terms of the movement of the body.

12 Claims, 3 Drawing Sheets

APPARATUS AND METHOD FOR DETECTING MOVEMENT OF AN OBJECT

This invention relates to apparatus for determining movement. The need for equipment capable of determining movement arises in a large number of situations such as navigation systems, stabilizers etc, and is usually fulfilled by means of a gyroscope. A conventional gyroscope is in the form of a rapidly spinning wheel set in a framework such that it is free to tilt in any direction. The wheel retains its original orientation regardless of the subsequent movement of the vehicle etc on which it is mounted. It therefore acts as a direction indicator from which the movement/direction of the vehicle can be established.

Conventional gyroscopes have several intrinsic disadvantages. The requirement for a rapidly spinning wheel makes them mechanically complicated, and difficult to set up. In addition the rotation of the wheel must be maintained, thereby requiring a driving force such as a motor or air jets.

It is an object of the present invention to provide an apparatus for the accurate determination of movement, which avoids the problems associated with the spinning wheel of a conventional gyroscope.

Accordingly there is provided apparatus for determining movement comprising a body, there being mounted on or in the body one or more sources and one or more detectors, the or each source being each adapted to propagate polychromatic light along a path to a detector, the or each detector being adapted to detect the intensity of incident radiation at a plurality of different wavelengths, and radiation modulation means supported by the body such that a change in the movement of the body in at least one direction causes a displacement of the radiation modulation means in the said path such as to vary the distributed spectral content of the light reaching the one or more detectors.

The change in the movement of the body detected by the apparatus may be movement applied to a body from a stationary position. The apparatus is therefore capable of acting as a vibration detector. Alternatively the change in the movement of the body may be a change in the velocity of the moving body, or a change in the direction of movement thereof. The apparatus is therefore additionally capable of acting as an accelerometer or a direction indicator, and can perform all the functions of a conventional, spinning wheel gyroscope.

The apparatus preferably includes means for analysing the variation in the distributed spectral content to determine the change in the movement of the body. Typically this is carried out by monitoring the ratio of intensities at two separate wavelengths of the light. In a preferred alternative, the one or more detectors each comprise at least first and second photo-responsive elements, the responsivity with respect to wavelength of the first element being different from that of the second, signals from the photo-responsive elements being fed to the analysis means which calculates, from the signals from the photo-responsive elements, the colour of the radiation incident on the one or more detectors as represented by two or more parameters on the Chromaticity (CIE) Diagram. In one convenient arrangement two different photo-responsive elements are employed, each with its own wavelength responsivity characteristic. Alternatively, one or both of the photo-responsive elements includes a coloured filter to impart a colour response characteristic, thereby allowing two identical photo-responsive elements to be employed, if desired. Preferably the responsivity with respect to wavelength of the at least first and second photo-responsive elements are such that their respective wavelength/intensity curves overlap for at least a part of the wavelength spectrum.

By employing at least first and second photo-responsive elements, a change in colour is determined by assessing the change in the whole of a selected part of the spectrum (colour modulation), as opposed to merely detecting the change at one or more selected wavelengths (wavelength modulation). Thus a change from colour A (represented by wavelength/intensity curve A) to colour B (represented by wavelength/intensity curve B) will be calculated from the area between the two curves, thereby giving a more complete analysis of "true" colour. Wavelength modulation, whilst giving an indication of the change, is limited in that it is a calculation based on the distance between the curves at selected wavelengths. Whichever method is employed, the monitored variation in the distributed spectral content is compared with calibrated measurements of the variations for different degrees and directions of movement of the body.

By the term 'polychromatic light' there is herein meant any multi-wavelength radiation, and is specifically meant to include both visible light and infra red radiation. The term 'colour', whilst used herein for ease of understanding, should in no way imply that only visible light may be employed. Where the apparatus employs a source emitting radiation outside of the visible spectrum, the term 'colour' will refer to the spectral distribution of the radiation.

There is conveniently mounted on or in the body at least two pairs of sources and detectors, each pair defining a polychromatic light path, the paths of at least two pairs being in different directions, the arrangement being such that a change in the movement of the body in either of at least two directions causes a displacement of the radiation modulation means in the path of at least one of the pairs of sources and detectors such as to vary the distributed spectral content of the light reaching the or each detector. With this arrangement, movement in two dimensions can be determined, the apparatus being capable of detecting movement in any direction in a predetermined plane. Conveniently the at least two pairs of sources and detectors are arranged such that the light path of each is in the same plane.

There is preferably provided at least three pairs of sources and detectors, each pair defining a polychromatic light path, the arrangement being such that a change in the movement of the body in any direction causes a displacement of the radiation modulation means in the path of at least one of the pairs of sources and detectors, such as to vary the distributed spectral content of the light reaching one or more of the detectors. Preferably, the paths of the at least three pairs are in different directions and the light path of the third pair is in a plane at an angle $\theta$ to that or those of the other two pairs (where $\theta \neq 0$), such an arrangement allows the detection of movement in three dimensions. Conceivably the radiation modulation means and the pairs of sources and detectors are such that a change in the movement of the body in any direction causes a displacement of the radiation modulation means in the path of at least two of the pairs of sources and detectors such as to vary the distributed spectral content of the light reaching two or more of the detectors.

Preferably the radiation modulation means and the pairs of sources and detectors are such that a change in the movement of the body in any direction causes a displacement of the radiation modulation means such as to produce a distributed spectral content of the light reaching the detectors which is unique for that direction of movement. The analysis means is therefore able to determine, from any particular combination of signals from the detectors, a single unambiguous value for both magnitude and direction of movement.

The radiation modulation means preferably comprises one or more filter elements which attenuate different wavelengths of light to a differing extent. Movement of the body causes a corresponding movement of the one or more filter elements thereby modulating the "colour" of the radiation reaching the one or more detectors. Analysis of the colour modulation can be used to determine the movement of the body. In one convenient arrangement the one or more filter elements comprise one or more coloured, transparent spheres, typically so-called ruby spheres. These spheres not only modulate the radiation but in addition help to focus it on to the one or more detectors, thereby providing a sharper resolution for the more accurate detection of very small amounts of movement.

The one or more spheres are conceivably suspended by means of one or more flexible elongate elements secured to the body. The one or more flexible elongate elements may be wires or elastic elements, and enable the one or more spheres to be mounted on the body in such a way as to allow movement with respect thereto in all three dimensions. Alternatively the one or more spheres are suspended by means of a plurality of jets of fluid, typically air, eminating from nozzles mounted on the body.

In an alternative arrangement the one or more filter elements comprise, or are mounted on, longitudinally extending members. Conveniently at least one of the one or more filter elements comprises an optical fibre. Alternatively or additionally at least one of the one or more filter elements comprises a filter strip, or comprises a coloured, transparent sphere mounted on a longitudinally extending member.

In one convenient arrangement at least one of the one or more longitudinally extending members is in the form of a cantilevered beam, secured to the body at or towards one or its ends with its other end free to move laterally of its longitudinal access. Movement of the body causes the free end of the cantilever beam to vibrate, producing a displacement of the radiation modulation means in the path of one or more pairs of sources and detectors. Alternatively one of the one or more longitudinally extending members is in the form of a cross-beam secured to the body at or towards both of its ends with its central portion free to move laterally of its longitudinal access. In another arrangement at least one of the one or more longitudinally extending members is suspended as described previously by means of one or more flexible elongate elements secured to the body.

Where the one or more filter elements comprise, or are mounted on, longitudinally extending members, movement of the body in the direction of the longitudinal axis of one of the filter elements may not result in a displacement of that filter element in the path of its pair of sources and detectors. Even where such a displacement does occur it may not result in a modulation of the light reaching the detector. Accordingly in such a case, the radiation modulation means conveniently comprises at least first and second filter elements each comprising, or mounted on, a longitudinally extending member, the longitudinal axis of the first filter element being in a different plane from that of the second filter element, the arrangement being such that a change in the movement of the body in at least one direction causes a displacement of the second filter element in the path of the third pair of sources and detectors, and a change in the movement of the body in another direction causes a displacement of the first filter element in the path of one or both of the first and second pairs of sources and detectors. By providing two filter elements with their longitudinal axes in different planes, even if the movement of the body is in the direction of the longitudinal axis of one of the filter elements, it will at least be transverse to the longitudinal axis of the other filter element.

The one or more sources are preferably adapted to produce a white light signal. The invention further resides in a method of determining movement employing apparatus as hereinbefore described. In particular, a method of determining a change of movement of a body comprises propagating polychromatic light along at least one light path to one or more detectors, supporting radiation modulation means such that a change in the movement of the body in at least one direction causes a displacement of the radiation modulation means in at least one light path such as to vary the distributed spectral content of the light reaching the or each detector, and calculating the change of movement of the body from the variation in the distributed spectral content of the light reaching the or each detector.

Embodiments of the invention will now be further described, by way of example only, with reference to the accompanying drawings, in which.

Figure 1:
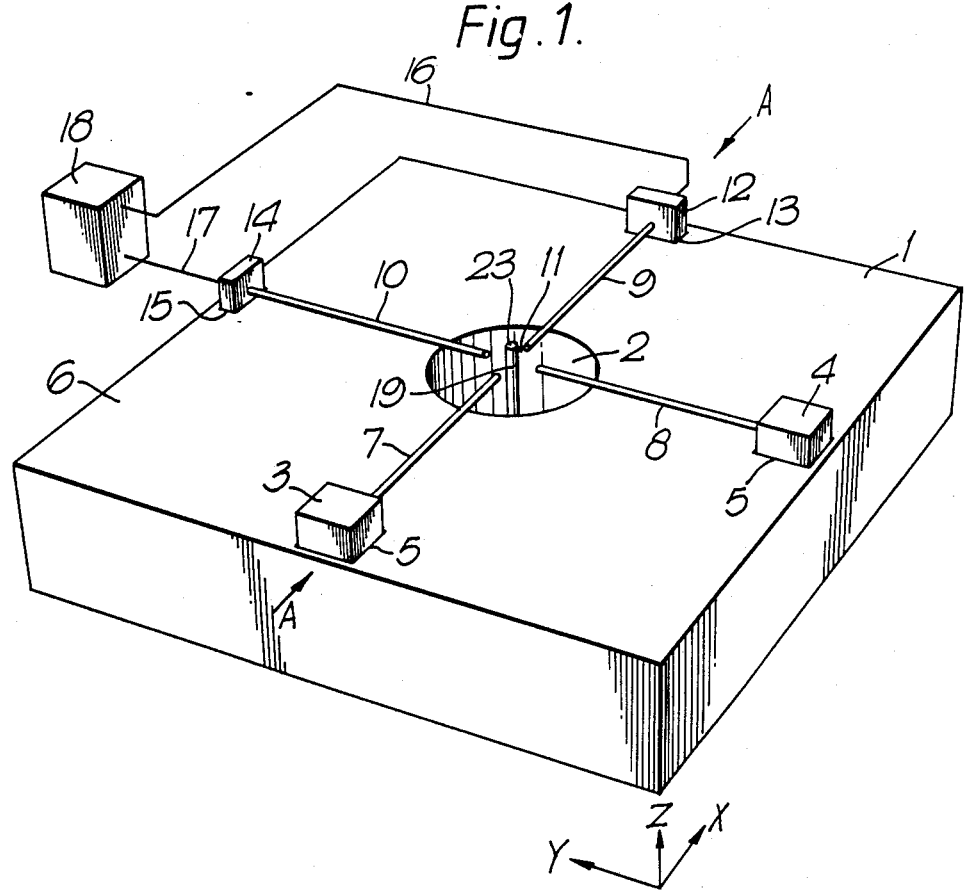
FIG. 1 is a perspective view of apparatus according to one embodiment of the invention.
Figure 2:
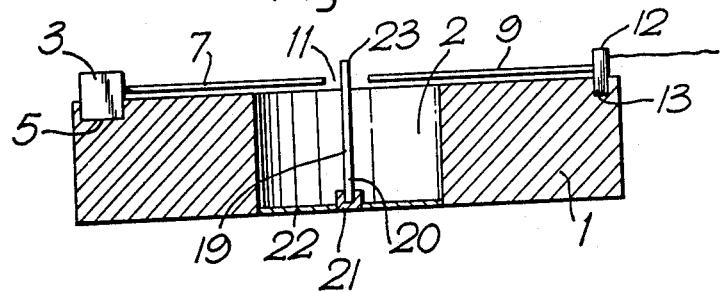
FIG. 2 is a cross-sectional view along the line A—A of FIG. 1.

Referring to FIGS. 1 and 2, there is shown a body in the form of a housing 1, being generally square in cross-section and having a circular aperture 2 extending longitudinally through its centre. Mounted on the housing 1 are two light sources 3 and 4, each source being received in a recess 5 which is present in the upper face 6 of the housing. Adjacent the source 3 is an optical fibre 7 which transmits light from the source 3 to the region of the aperture 2. On the opposite side of the aperture 2 is another optical fibre 9, in alignment with the fibre 7 and spaced therefrom to leave a gap 11. At the end of the fibre 9 remote from the gap 11 is a detector in the form of a charge coupled device (CCD) array 12, the array 12 being received in a corresponding recess 13 in the housing 1. In similar manner optical fibres 8 and 10 transmit light from the source 4, across the gap 11 and to a CCD array 14 received in a recess 15 in the housing. Arrays 12 and 14 are in communication via lines 16 and 17 with a microprocessor 18, shown in FIG. 1 to be external to the housing 1 but which may equally be mounted directly thereon.

A cantilevered optical fibre 19 is present in the gap 11, the longitudinal axis of the cantilevered fibre 19 being orthogonal to those of the fibres 7 and 9, and 8 and 10. The cantilevered fibre 19 is secured at its lower end 20 in a U-shaped support 21. The support 21 is mounted in a base plate 22, the base plate acting as a closure for the aperture 2 and as a mechanical linkage between the body 1 and the lower end 20 of the cantilevered fibre 19. In the event of flexing of the cantilever fibre 19 the upper end 23 thereof is free to move in the gap 11.

The operation of the device of FIGS. 1 and 2 will now be described. Polychromatic light from the source 3, is transmitted to the array 12 along a first light path constituted by the optical fibres 7 and 9, the light path extending across the gap 11 and through the cantilevered fibre 19. Similarly light from the source 4 travels along a second light path constituted by optical fibres 8 and 10, also including the gap 11 and cantilevered fibre 19. The light passing through the cantilevered fibre 19 undergoes colour modulation in that the spectral content of the light is changed by the attenuation of some wavelengths to a greater or lesser degree than the attenuation of others. Incident light is detected by the arrays 12 and 14 and signals are passed to the microprocessor 18 which calculates the intensity of light of selected wavelengths received by the arrays. Microprocessor 18 determines a factor of the wavelength modulation such as the ratio of the intensities of light received at two different wavelengths.

A change in the movement of the body 1, whether due to a vibration applied thereto, a change in the velocity of the body, or a change in the direction of the movement thereof, causes a flexing of the cantilevered fibre 19. A component of movement in the X-direction, as shown in FIG. 1 causes the upper end 23 of the cantilevered fibre to move laterally of the light path between optical fibres 8 and 10. Similarly a component of movement in the Y-direction causes the upper end 23 to move laterally of the light path between optical fibres 7 and 9. Movement of the cantilever fibre in one or both of the light paths varies the colour modulation of the light reaching the CCD arrays. The microprocessor 18 monitors the change in the factor of the wavelength modulation and compares this with predetermined calibrated values for known changes of movement. In this way the change in wavelength modulation is interpreted as a calculation of the movement of the housing 1. The device of FIGS. 1 and 2 is therefore capable of detecting any change of movement in the plane containing the X and Y directions.

Figure 3:
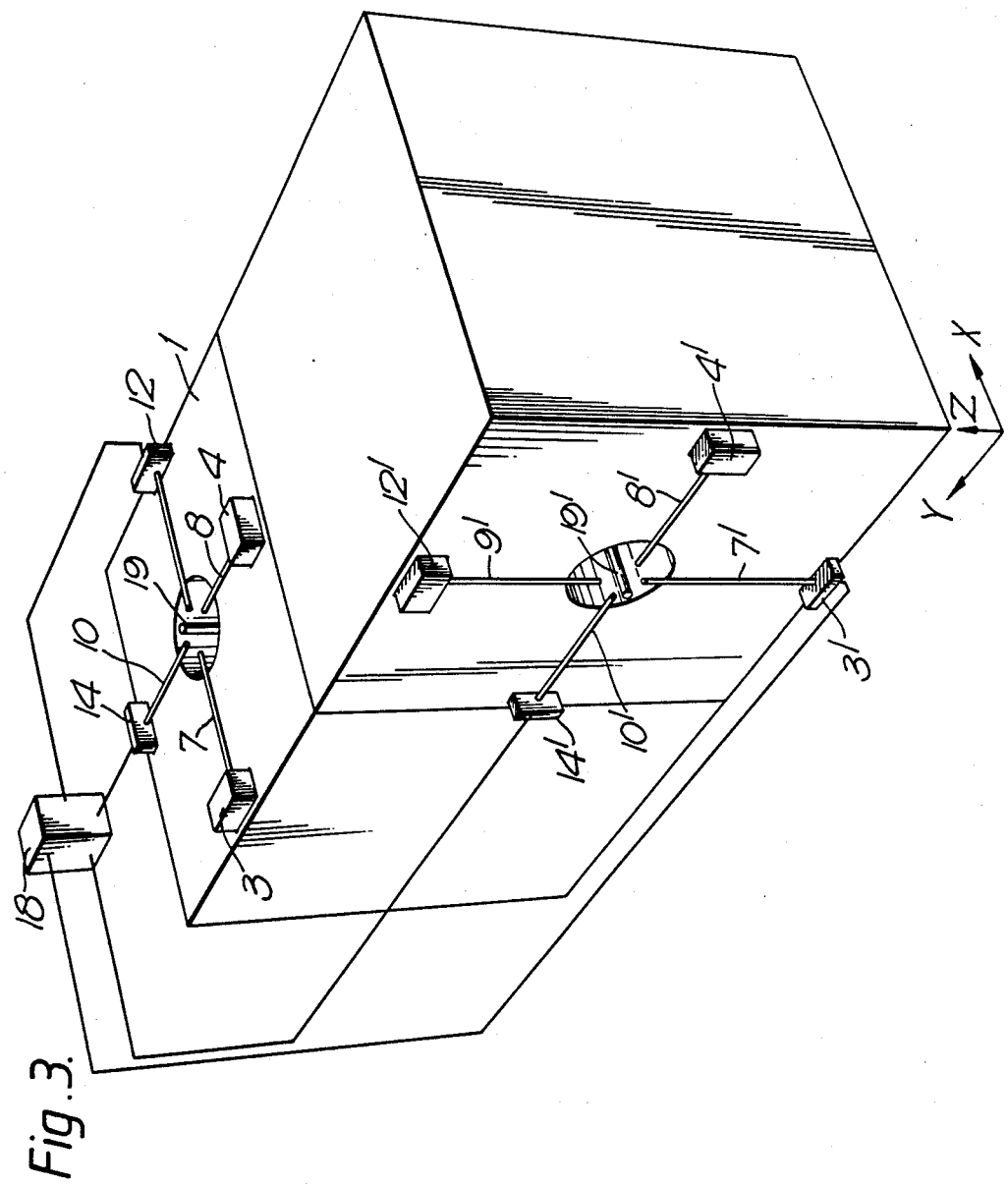
FIG. 3 is a perspective view of apparatus according to an alternative embodiment of the invention.

A component of movement in the Z-direction will not produce flexing of the cantilever fibre 19 and hence will not be detected. If it is desired to monitor movement in three dimensions, the device such as that of FIG. 3 may be employed. The device of FIG. 3 is based on that of FIG. 1, and similar components are designated with a like reference numerals. The housing 1 and associated elements are enhanced by the provision of an additional housing 1', together with a cantilevered optical fibre 19', rotated through 90° with respect thereto. This means that the longitudinal access of the cantilever fibre 19' lies along the axis of the X-direction, as opposed to the Z-direction as does the cantilever fibre 19. Therefore any component of movement in the Z-direction applied to the housings 1 and 1', which are secured for movement one to the other, will produce a flexing of the cantilevered fibre 19' so that it moves laterally of the light path between optical fibres 8' and 10'. The light path between optical fibres 7' and 9', the presence of which is not strictly essential, serves as a corroboration to the movement in the Y-direction detected by the light path between optical fibres 7 and 9. With the arrangement of FIG. 3, a change of movement in any direction will produce a flexing of at least one of the fibres 19 and 19', which flexing can be analysed by the microprocessor 18 to calculate the extent and/or direction of the movement.

Figure 4:
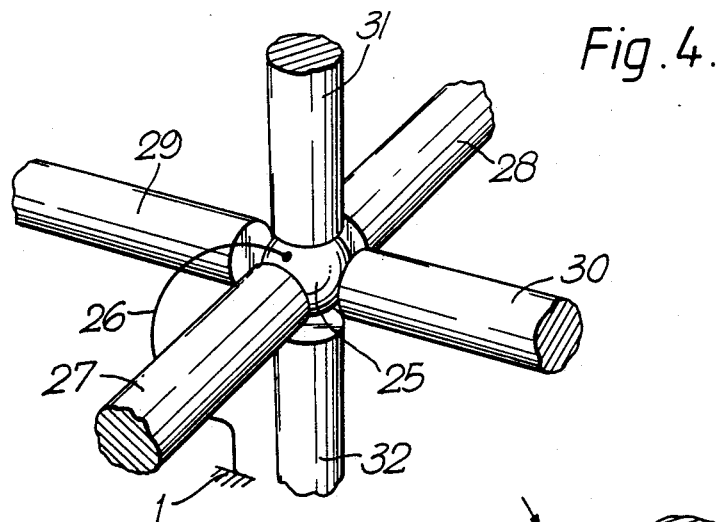
FIGS. 4 to 6 are schematic diagrams of a part of apparatus according to other alternative embodiments of the invention.
Figure 5:
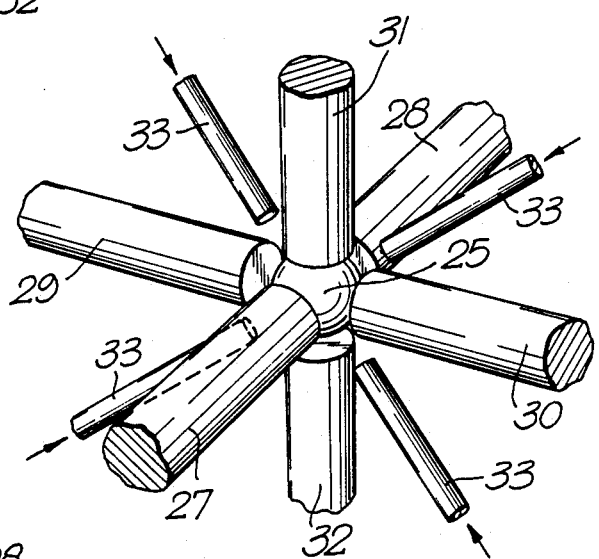
Figure 6:
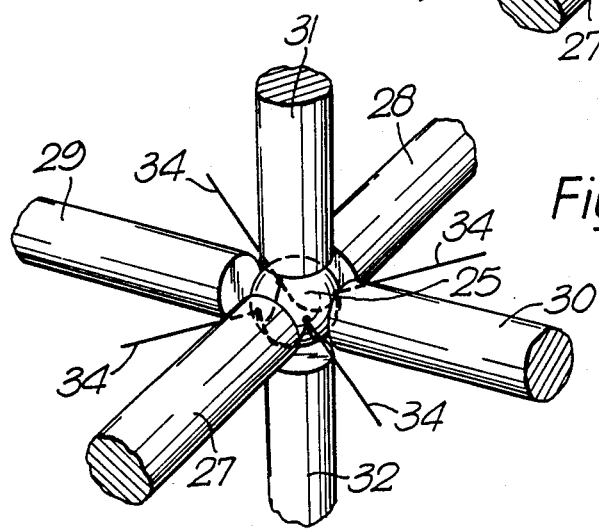

FIGS. 4 to 6 show embodiments of the invention in which the cantilevered optical fibre is replaced by a ruby sphere 25. The ruby sphere, like the optical fibre, serves to focus the light from the sources so as to increase the sensitivity of the apparatus. Additionally, as the sphere performs colour modulation on light passed therethrough in any direction, suitable mounting of the sphere allowing movement in three dimensions permits the calculation of movement in any direction from a single sphere, rather than requiring two optical elements as in FIG. 3.

FIG. 4 shows the mounting of the ruby sphere 25 by means of a cantilever wire 26. The wire is secured to the body 1 at one of its ends and sphere 25 is secured at the other. Three pairs of optical fibres, 27 and 28, 29 and 30, and 31 and 32, provide three light paths through the sphere 25, in three mutually perpendicular directions. The wire 26 is arched to allow fibres access to the sphere. A change in the movement of the housing 1 causes the sphere 25 to be displaced in one or more of the light paths between the optical fibres. As before this displacement results in colour modulation of the light signals, which can be used to calculate the movement of the housing.

FIG. 5 shows an arrangement in which the ruby sphere 25 is supported by means of air jets eminating from nozzles 33. This again allows unrestricted access to the sphere, yet leaving it free to be displaced in any direction.

FIG. 6 shows the ruby sphere 25 suspended by means of flexible elements such as wires 34. The wires are attached to the sphere in such a manner as to permit movement in any direction, whilst allowing an unobstructed passage through the sphere for the light paths from the optical fibres 27 to 32.

It will be appreciated that modifications to the aforementioned apparatus may be made without departing the scope of the present invention. For example, the focusing effect of a ruby sphere may enable calculations of movement in three dimensions to be made without the need for three pairs of sources and detectors, movement longitudinally along a light path resulting in colour modulation due to the change in focus of the transmitted beam. Another modification, appropriate where vibration of a predetermined frequency is to be detected, is to mount the radiation modulation means on a member such as a diaphragm, the natural resonant frequency of the diaphragm being that of the predetermined frequency to be detected. Vibration at the predetermined frequency results in a much greater displacement of the radiation modulation means than vibration at other frequencies. These and other modifications will be apparent to those skilled in the art as available alternatives, each in accordance with the present invention.

What I claim as my invention is:

1. Apparatus for determining movement comprising: a body; at least one detector; at least one source for propagating polychromatic light along a path to the detector, the source and the detector each being mounted on or in the body, the detector comprising at least first and second photo-responsive elements, the responsivity with respect to wavelength of the first element being different from that of the second; radiation modulation means supported by the body such that a change in the movement of the body in at least one direction causes a displacement of the radiation modulation means in the said path such as to vary the distributed spectral content of the light reaching the one or more detectors; and analysis means for calculating, from the signals from the photo-responsive elements, the colour of the radiation incident on the one or more detectors as represented by two or more Chromaticity (CIE) Diagram parameters, so as to determine the change in the movement of the body.

2. Apparatus according to claim 1 comprising at least two pairs of sources and detectors for defining at least two polychromatic light paths, the at least two pairs of sources and detectors being mounted on or in the body such that the paths of the at least two pairs are in different directions, the arrangement being such that a change in the movement of the body in either of at least two directions causes a displacement of the radiation modulation means in the path of at least one of the said pairs of sources and detectors such as to vary the distributed spectral content of the light reaching at least one of the detectors.

3. Apparatus according to claim 1 comprising at least a first pair, a second pair, and a third pair of sources and detectors for defining at least three polychromatic light paths, the arrangement being such that a change in the movement of the body in any direction causes a displacement of the radiation modulation means in the path of at least one of the pairs of sources and detectors, such as to vary the distributed spectral content of the light reaching at least one of the detectors.

4. Apparatus according to claim 3 including a first pair, a second pair, and a third pair of sources and detectors mounted on or in the body such that the paths of the at least three pairs are in different directions and the light path of the third pair is in a plane at an angle $\theta$ to that or those of the other two pairs (where $\theta \neq 0$).

5. Apparatus according to claim 4 wherein the radiation modulation means and the pairs of sources and detectors are mounted on or in the body such that a change in the movement of the body in any direction causes a displacement of the radiation modulation means in the path of at least two of the pairs of sources and detectors such as to vary the distributed spectral content of the light reaching at least two of the detectors.

6. Apparatus according to claim 4 wherein the radiation modulation means and the pairs of sources and detectors are mounted on or in the body such that a change in the movement of the body in any direction causes a displacement of the radiation modulation means such as to produce a distributed spectral content of the light reaching the detectors which is unique for that direction of movement.

7. Apparatus according to claim 1 wherein the radiation modulation means comprises at least one filter element for attenuating different wavelengths of light to a differing extent.

8. Apparatus according to claim 7 wherein the at least one filter element comprises at least one coloured, transparent sphere.

9. Apparatus according to claim 8 wherein the at least one sphere is suspended by means of at least one flexible elongate element secured to the body.

10. Apparatus according to claim 7 wherein the at least one filter element comprises, or is mounted on, at least one longitudinally extending member.

11. Apparatus according to claim 3 wherein the radiation modulation means comprises at least first and second filter elements each comprising, or mounted on, a longitudinally extending member, the first and second filter elements being mounted on or in the body such that the longitudinal axis of the first filter element is in a different plane from that of the second filter element, the arrangement being such that a change in the movement of the body in at least one direction causes a displacement of the second filter element in the path of the third pair of sources and detectors, and a change in the movement of the body in another direction causes a displacement of the first filter element in the path of at least one of the first and second pairs of sources and detectors.

12. A method of determining a change of movement of a body comprising propagating polychromatic light along at least one light path to at least one detector comprising at least first and second photo-responsive elements, the responsivity with respect to wavelength of the first element being different from that of the second, supporting radiation modulation means such that a change in the movement of the body in at least one direction causes a displacement of the radiation modulation means in at least one light path such as to vary the distributed spectral content of the light reaching the at least one detector, and calculating, from the signals from the photoresponsive elements, the colour of the radiation incident on the one or more detectors as represented by two or more Chromaticity (CIE) Diagram parameters so as to determine the change of movement of the body.

* * * * *